US007165422B2

(12) United States Patent
Little

(10) Patent No.: US 7,165,422 B2
(45) Date of Patent: Jan. 23, 2007

(54) SMALL-SCALE GAS LIQUEFIER

(75) Inventor: William A. Little, Palo Alto, CA (US)

(73) Assignee: MMR Technologies, Inc., Mountain View, CA (US)

( * ) Notice: Subject to any disclaimer, the term of this patent is extended or adjusted under 35 U.S.C. 154(b) by 0 days.

(21) Appl. No.: 11/265,025

(22) Filed: Nov. 2, 2005

(65) Prior Publication Data

US 2006/0130519 A1 Jun. 22, 2006

Related U.S. Application Data

(60) Provisional application No. 60/626,221, filed on Nov. 8, 2004.

(51) Int. Cl.
*F25J 1/00* (2006.01)
*F25B 19/00* (2006.01)
*A61M 11/00* (2006.01)

(52) U.S. Cl. .......................... 62/613; 62/615; 62/51.1; 128/201.21

(58) Field of Classification Search ...................... 62/6, 62/51.1, 611, 615, 613; 128/201.21
See application file for complete search history.

(56) References Cited

U.S. PATENT DOCUMENTS 5,678,425 A 10/1997 Agrawal et al. .............. 62/646
5,836,173 A 11/1998 Lynch et al. .................. 62/613
5,979,440 A * 11/1999 Honkonen et al. ...... 128/201.21
6,212,904 B1 * 4/2001 Arkharov et al. ............. 62/615
6,298,688 B1 10/2001 Brostow et al. .............. 62/613
6,591,632 B1 7/2003 Mahoney ...................... 62/613
6,698,423 B1 * 3/2004 Honkonen et al. ...... 128/201.21
6,751,984 B1 * 6/2004 Neeraas et al. ............... 62/612
6,910,350 B1 6/2005 Brigham et al. .............. 62/643
2004/0045315 A1 * 3/2004 Kamoshita et al. ........... 62/615

* cited by examiner

*Primary Examiner*—William C. Doerrler
(74) *Attorney, Agent, or Firm*—Lumen Intellectual Property Services, Inc.

(57) ABSTRACT

A cryogenic gas is liquefied using a refrigeration system [101] thermally coupled at an evaporator [125] to a cold end of a gas supply system [103] within a dewar [116]. The refrigerator has a minimum temperature at an evaporator [125] above the boiling point of the gas at atmospheric pressure but below the boiling point of the gas at a high pressure. Thus, the gas is compressed [128] to high pressure so it condenses when cooled by the evaporator [125]. As it expands at a flow restrictor [148], a portion evaporates and cools a fraction to the temperature of the boiling point of the gas at atmospheric pressure, producing liquefied gas. Opening a purge valve [142] sends warm gas upward through heat exchange section [146] and out through a three-way valve [138] for defrosting. To reduce clogging, the gas supply valve [138] is controlled by a gas purity sensor [158].

18 Claims, 3 Drawing Sheets

SMALL-SCALE GAS LIQUEFIER

CROSS-REFERENCE TO RELATED APPLICATIONS

This application claims priority from U.S. provisional patent application No. 60/626,221 filed 8 Nov. 2004, which is incorporated herein by reference.

FIELD OF THE INVENTION

The present invention relates generally to techniques for the liquefaction of cryogenic gasses such as nitrogen, oxygen, argon, methane, and other similar low-boiling-point substances. More specifically, it relates to small-scale cryogenic gas liquefiers that are inexpensive and simple to operate.

BACKGROUND OF THE INVENTION

Shortly after nitrogen and oxygen were first liquefied in the last 1800's, industrial production of liquid nitrogen and liquid oxygen was accomplished and they rapidly became important commodities for the steel and fertilizer industries. Economies of scale reduced the cost of liquid nitrogen and liquid oxygen to a few cents per liter. Thousands of tons of each are now produced per day for industrial purposes and are transported over large distances in tanker cars. They are also available to a wide class of users, in particular, those in university and industrial research laboratories, medical clinics and hospitals, world-wide. However, the quantities used by such individual researchers and doctors in these establishments are usually small, of the order of a few liters per day. While the cost of these cryogens at the source is small, distribution, storage losses and costs of purchasing in small quantities results in an end price substantially larger than the bulk price. This issue was partially addressed in the 1950's by the development of a laboratory scale closed cycle gas refrigeration machine as described by J. W. H. Kohler and C. O. Jonkers, in *Philips Techn. Rev.* 16, 69 (1954). These machines were much smaller than the large industrial liquefiers for liquefaction of air or nitrogen, but were not office machines. They draw almost 6 kW of power and produce over 140 liters of liquid air per day. This is several orders of magnitude larger than what would be needed for a doctor's office, or an individual researcher. A need has existed, therefore, for a much smaller liquefier capable of generating a few liters per day that could address the liquid nitrogen needs of dermatologists, materials scientists and chemists; the liquid oxygen needs for breathing-impaired patients; and needs for small quantities of other liquid cryogens.

SUMMARY OF THE INVENTION

A dramatic improvement in the efficiency and reliability of a new class of low-cost cryogenic coolers, Kleemenko cycle coolers, opens the possibility that some of the problems discussed above may be overcome. These new coolers, however, can not be adapted for these liquefaction purposes without attending to several issues. For example, when used as liquefiers, these coolers have a number of limitations that demand a different approach for the liquefaction of gases from that of traditional industrial liquefiers. Furthermore, their use in an office environment introduces special safety and handling concerns different from those in an industrial environment. In addition, the small scale of the machine and mode of operation imposes other constraints on the implementation of the liquefaction process. On the other hand, this difference in scale enables the use of novel means for addressing some of the classic problems of the liquefaction of gases such as nitrogen, oxygen, argon and natural gas. The present invention includes the design of a small gas liquefier that takes these various factors in to account and enables the construction of a practical device that meets the needs of the market.

According to one embodiment, the design and construction of an office, or home scale cryogenic liquefier makes possible the safe, efficient, and convenient liquefaction of nitrogen, oxygen, natural gas, and some other gases. An enabling technology for the development of such a liquefier is the successful implementation of a refrigeration system using a multi-component, mixed refrigerant, single-stream, cascade, throttle-expansion refrigeration cycle, known as the "Kleemenko-cycle" after its originator A. P. Kleemenko, who first described this refrigeration cycle in *Proceedings of the Xth International Congress of Refrigeration, Copenhagen* 1, 34–39 (1959), Pergamon Press, London. Improving on Kleemenko's ideas, W. A. Little in U.S. Pat. No. 5,617,739 (1997), and W. A. Little and I. Sapozhnikov, in U.S. Pat. No. 5,724,832 (1998), developed self-cleaning techniques that enable these systems to operate continuously for tens of thousands of hours at cryogenic temperatures with no change in performance or need for maintenance, as documented in Little, W. A., *Kleemenko Cycle Coolers: Low Cost Refrigeration at Cryogenic Temperatures,* Proc. Seventeenth International Cryogenic Engineering Conference, Eds. D. Dew-Hughes, R. G. Scurlock, and J. H. P. Watson, Institute of Physics Publishing, Bristol (1998), 1–9, and in Little, W. A., *MMR's Kleemenko Cycle Coolers: Status, Performance, Reliability, and Production.* M-CALC IV, Fourth Workshop on Military and Commercial Applications of Low-Cost Cryocoolers, Strategic Analysis, Inc., Nov. 20–21, 2003. The use of common domestic refrigerator components, such as compressors, copper fittings, condensers, and such like, in the fabrication of the coolers have brought the cost of the cryogenic system close to that of home refrigeration systems. In addition, the design of efficient refrigerant mixtures based on ideas of A. P. Kleemenko and implemented using a procedure described by W. A. Little in U.S. Pat. No. 5,644,502 (1997), and similar procedures described by J. Dobak et al. in U.S. Pat. No. 5,787,715 (1998), has dramatically increased the efficiency of these coolers enabling a significant reduction in the size of the device. Accordingly, the above referenced patents are hereby incorporated by reference.

In one aspect of the invention, a method for the liquefaction of a gas is provided. The method includes purifying the gas, cooling the purified gas to produce condensed gas, collecting the condensed gas in a thermally insulated region, and dispensing the condensed gas from the thermally insulated region through a dispensing line. When cooling the gas, the temperature of the gas is reduced using a cryogenic refrigerator having a minimum temperature above a boiling point of the gas at atmospheric pressure and below a boiling point of the gas at the high pressure. The gas is compressed so that the purified gas has a pressure above atmospheric pressure and thus condenses when cooled. The condensed gas is expanded to atmospheric pressure to evaporate a portion of the condensed gas and cool a fraction of the condensed gas to the boiling point of the gas at atmospheric pressure. The gas may be cooled by a pulse-tube, Stirling, Gifford-McMahon, or Kleemenko-cycle cryogenic refrigerator. The temperature of the gas may be reduced by thermally coupling the gas to a counter-current heat exchanger of the refrigerator. In one embodiment, the cold section of the gas line may be cleaned by intermittently opening a purge valve allowing the purified gas to flow through a warm purge line, sending the warm gas from the warm purge line upward through a cold end of a gas supply line, and venting the warm gas from the gas supply line out through a three-way valve. In addition, to help reduce clogging of the cold end of the gas supply line, purifying the gas may include passing the gas through a pressure swing absorber and a membrane separator, sensing a level of gas purity at the membrane separator, and controlling the flow of purified gas into the cold end of the gas supply line in dependence upon a sensed level of gas purity. Dispensing the condensed gas may be performed by opening a dispense valve that allows gas to flow into the thermally insulated region, forcing the liquid out through a dispensing line. Preferably, the gas is reduced in pressure prior to entering the thermally insulated region. For safety, a user key may be required to enable dispensing of the condensed gas. By sensing a proximity of a dispense dewar and requiring a sensed presence of the dispense dewar to enable dispensing, additional safety may be provided.

In another aspect, a device for liquefaction of a gas is provided. The device includes a thermally insulated region (e.g., a dewar) in which the gas is liquefied and collected. The device also has a gas supply system with a first section that provides a purified stream of gas to a gas supply line in a second section where it is cooled and condensed. The first section is outside the thermally insulated region while the second section is within the thermally insulated region. Similarly, the device includes a cryogenic refrigerator which has a warm section outside the thermally insulated region and a cold section inside the thermally insulated region. The cold section is thermally coupled to the second section of the gas supply system to cool the purified stream of gas. A dispensing line with an input end within the thermally insulated region and an output end outside the thermally insulated region is also included in the device. A compressor in the first section of the gas supply system compresses the gas so that the purified stream of gas has a high pressure above atmospheric pressure when it enters the second section where it is cooled by the cold section of the cryogenic refrigerator. The cold section has a minimum temperature above a boiling point of the gas at atmospheric pressure and below a boiling point of the gas at the high pressure. In the second section of the gas supply system, the condensed gas flows through a flow restrictor where the pressure drops from the high pressure to atmospheric pressure. A portion of the purified stream of gas evaporates, cooling a fraction of the purified stream of gas to the boiling point of the gas at atmospheric pressure. This condensed fraction is then collected and stored at atmospheric pressure for subsequent dispensing, as desired. The cryogenic refrigerator may be a pulse-tube, Stirling, Gifford-McMahon, or Kleemenko-cycle cryogenic refrigerator. The cold section of the cryogenic refrigerator may include a counter-current heat exchanger thermally coupled to a heat exchanger section of the second section of the gas supply system. A warm purge line connected directly to a cold end of the gas supply line may be included in the second section, and a purge valve in the first section may be provided to control the flow of warm gas into the warm purge line. A three-way valve in the first section allows the warm gas to flow upward through the gas supply line and vent outside the insulated region. The first section of the gas supply system may be implemented using a pressure swing absorber and a membrane separator. In addition, the device may include a hygrometer connected to the membrane separator, and a valve connected to the hygrometer to control the flow of gas to the second section of the gas supply system in dependence upon a level of gas purity detected by the hygrometer. To dispense the condensed gas out through the dispense line, the first section of the gas supply system may be provided with a dispense valve that allows pressurized gas to flow into the thermally insulated region and a pressure regulator that reduces the pressure of the gas prior to entering the thermally insulated region. A key lock may be connected to the dispense valve as a safety measure, so that the key lock prevents the dispense valve from opening when locked and allows the dispense valve to be opened when unlocked by a user key. In addition, a proximity sensor may be connected to the dispense valve such that the proximity sensor prevents the dispense valve from opening when a dispense dewar is not sensed and allows the dispense valve to be opened when a dispense dewar is sensed.

DETAILED DESCRIPTION

Figure 1A:
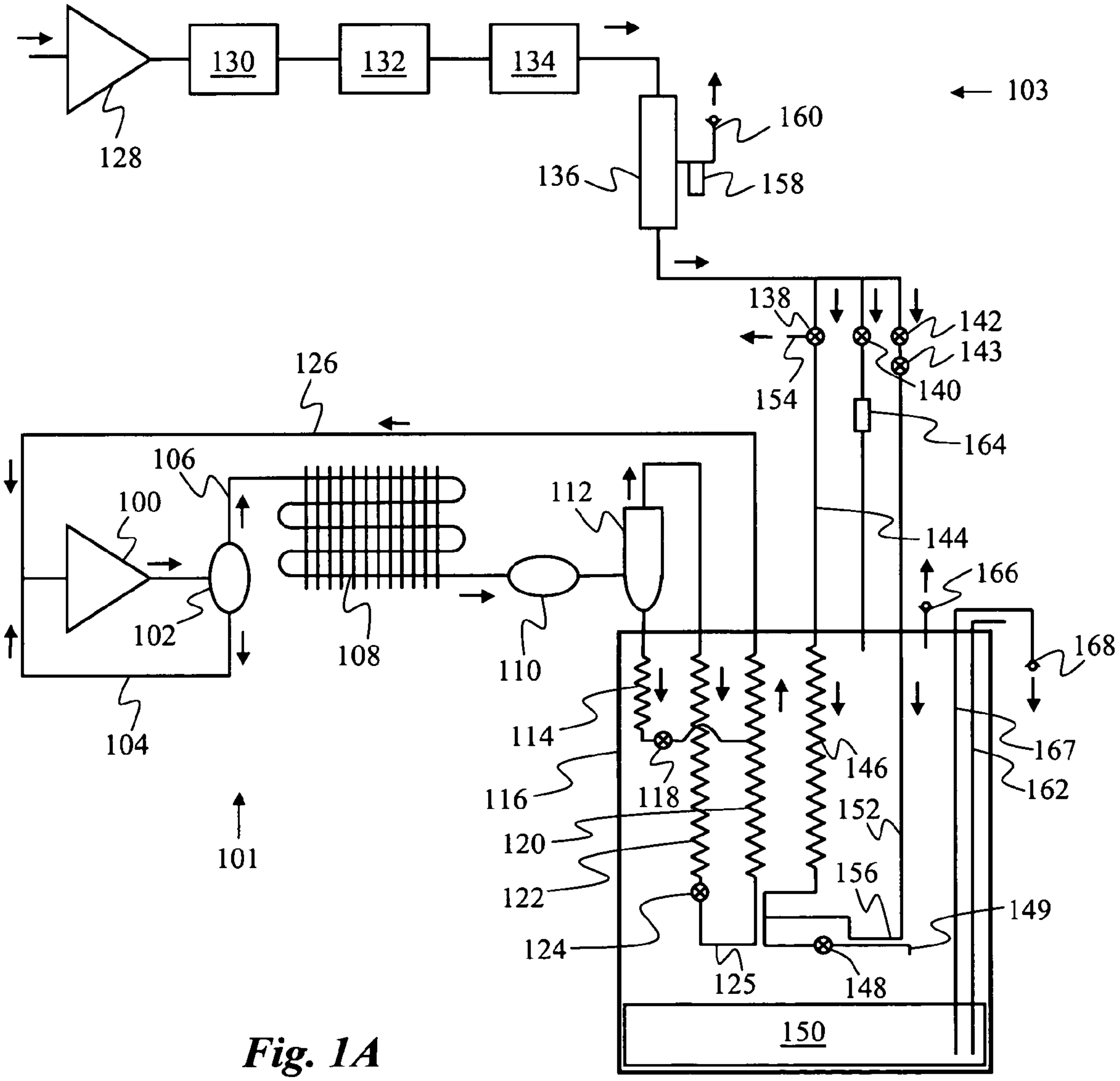
FIG. 1A is a schematic of a device for the liquefaction of nitrogen, according to an embodiment of the invention.

A schematic of a device for the liquefaction of nitrogen according to a preferred embodiment of the invention is shown in FIG. 1A. Although the following description will focus on a device designed for the liquefaction of nitrogen, a the device may also be used for the liquefaction of oxygen or the other cryogenic gases. In such cases, the operating temperature is suitably adjusted and the refrigerant mixture is optimized to match the liquefaction temperatures of the particular gas to be liquefied.

We consider now the nitrogen liquefier device. The device has a nitrogen gas supply system 103 which has a first section outside dewar 116 where the gas is purified and compressed and a second section inside dewar 116 where the gas is cooled and condensed. Similarly, a cryogenic refrigeration system 101 has a warm section outside dewar 116 where the refrigerant is compressed and a cold section inside dewar 116 where the refrigerant expands and provides cooling. The refrigeration system is based on the classic Kleemenko cycle cooler. A suitable refrigerant enters an oil-lubricated hermetically sealed compressor 100, such as used in a home refrigerator, where it is compressed. The compressed refrigerant then enters an oil separator 102 that captures most of the oil entrained in the refrigerant stream from the compressor and returns the oil to the compressor through a capillary tube 104. Meanwhile, the warm refrigerant vapor passes out the top of the separator through a tube 106 to an air-cooled condenser 108. In condenser 108 some of the refrigerant condenses as a liquid to produce a two-phase stream which then passes through a filter-drier 110 that removes traces of moisture. The refrigerant stream then enters a second liquid-vapor separator 112. The upper portion of separator 112 contains a fractionating column of many plates, and the lower portion contains a cyclone separator for removing any remaining oil and the condensed refrigerant. Separator 112 is preferably a device such as described in U.S. Pat. No. 5,617,739 and U.S. Pat. No. 5,724,832. The separated liquid component passes out through the bottom of separator 112 into a heat exchanger section 114 in the liquefaction dewar 116. After passing through heat exchanger section 114, the liquid expands through a flow restrictor 118 and joins with fluid passing though an upper portion of a counter-flow heat exchanger section 120. In this embodiment, the flow restrictor 118 is located about one third of the way down the heat exchanger section 120 at a point where the temperature will ultimately fall to about 213 K (−60° C.). The evaporating liquid coming out of flow restrictor 118 and up through heat exchanger section 120 helps to pre-cool a separated vapor stream from the top of separator 112 as it flows down through heat exchanger section 122. Some of the vapor condenses as it passes down heat exchanger section 122. At flow restrictor 124 the cooled refrigerant stream drops in pressure and flows through evaporator 125, where the cold refrigerant cools the load (i.e., the bottom of heat exchanger section 146 which is thermally coupled to evaporator 125), and the cold refrigerant fluid then moves up heat exchanger section 120, cooling the incoming vapor stream flowing down section 122. After exiting the dewar, the refrigerant is returned to the compressor 100 through fluid line 126 to be re-compressed and re-circulated.

TABLE 1

Kleemenko Cycle Refrigerant Mixture for nitrogen liquefier.

| Component | Mole Fraction |
|---|---|
| Neon | 0.04 |
| Nitrogen | 0.38 |
| Methane | 0.25 |
| R14 | 0.11 |
| Ethane | 0.09 |
| Propane | 0.04 |
| so-Butane | 0.04 |
| so-Pentane | 0.05 |
| | 1.00 |

A suitable refrigerant for the liquefaction of nitrogen using the device described above is given in Table 1. This particular refrigerant is designed to have a large refrigeration capacity at about 95 K (−178° C.). The refrigeration capacity of Kleemenko-cycle coolers drops dramatically as the operating temperature is reduced below about 90 K because the small latent heat of evaporation of refrigerant components with boiling points near 90 K and the rapid fall of the vapor pressure of these liquids below this temperature limits the refrigeration capacity in this temperature region. This fact dictates a different procedure for the liquefaction of nitrogen and to a lesser extent, oxygen, too. The boiling point of nitrogen at one atmosphere pressure is 77.4 K. At this temperature the refrigeration capacity of the Kleemenko cycle refrigerator is small compared to what it can have in the range between 90 K to 100 K. This is a limitation of the Kleemenko cycle cooler. Other types of cryocoolers such as the Pulse-Tube, Gifford-McMahon, and Stirling cycle coolers are not so limited. Therefore, in order to obtain efficient liquefaction of nitrogen with the Kleemenko cycle cooler, the nitrogen is condensed at a relatively high pressure of 507 kPa to 709 kPa (5 to 7 atm). Thus, the cold section of the cryogenic refrigerator has a minimum temperature above the boiling point of the nitrogen gas at atmospheric pressure but below the boiling point of the gas at the high pressure. How this is implemented is shown in FIG. 1.

For the liquefaction of nitrogen, air enters a compressor 128 where it is compressed to a pressure of about 811 kPa (8 atm). The compressed air is then passed through a pre-filter 130 and a coalescing trap 132 with an automatic drain to remove water, then to a pressure swing absorber 134 to dry the gas further and remove carbon dioxide. The dry and partially purified air from pressure swing absorber 134 then enters a membrane separator 136 where oxygen is removed from the nitrogen. A stream of dry, purified nitrogen from membrane separator 136 then enters a manifold comprising three control valves 138, 140, 142 associated with three corresponding flow lines. Valve 138 is a 3-way valve. In one setting, it allows nitrogen to pass into dewar 116 through a nitrogen supply line 144. The cold end of supply line 144 within dewar 116 is a heat exchanger section 146, which is formed of a small diameter (1.5 mm OD, 1.0 mm ID) tube that is wound round the Kleemenko cycle heat exchanger sections 120 and 122. The nitrogen gas is precooled to about 100 K as it flows down heat exchanger section 146. At the bottom of the heat exchanger section 146 the tube is wound round the evaporator 125 of the Kleemenko refrigerator, where the nitrogen gas is cooled and condenses to form liquid nitrogen. Because the nitrogen is pressurized, it condenses at the evaporator 125 between 90 K and 100 K. The liquid nitrogen then passes through flow restrictor 148, where the pressure drops to about 101 kPa (1 atm) and a fraction of the liquid nitrogen evaporates, cooling a remaining fraction of the nitrogen to its boiling point temperature (about 78 K) at the pressure of the gas in the dewar, i.e., at about 101 kPa (1 atm). The liquid fraction then exits through an opening 149 and collects in the dewar as the desired liquid nitrogen 150.

The flow-restrictor 148 can be an adjustable valve (manual or electronic), a fixed orifice, a porous metal plug, a long capillary tube, or a short small diameter capillary tube. An adjustable valve allows one to optimize the performance of the device. But where the user has no interest in the workings of the device and simply needs the liquid nitrogen, all such adjustments are preferably avoided in the design. For optimal reliability, the flow restrictor 148 is preferably a short length (15 cm) of a small diameter capillary tube (ID 0.025 cm). The small diameter of the tube is designed to limit the flow of gas during the cool-down stage where the flow velocity is limited by the speed of sound of the nitrogen. The low flow places a smaller load on the cooler during this phase of the process. When the temperature reaches the condensation temperature of the nitrogen, liquid forms and the mass flow increases as the high density liquid can readily pass through the capillary. The short capillary is superior to the orifice flow restrictor, as some adjustment to the flow characteristics can be made during design by varying the length of the tube.

In order to reduce the boil-off rate of the dewar, it is preferable that the dewar have a small-diameter neck. An effective way to reduce this diameter is to use a nitrogen supply line of small diameter. A small diameter line also results in a higher flow velocity in the tube for the incoming nitrogen, and better heat transfer. Although a small diameter line can be clogged more readily by frozen moisture or carbon dioxide, it is possible to operate the liquefier successfully even with less than perfect removal of water and carbon dioxide from the nitrogen feed. In fact, the liquefier described above can continue to liquefy for more than several days with only a small loss of the liquid nitrogen yield due to build-up of contaminants in the nitrogen pre-cooling line. To operate the liquefier continuously for longer periods, contaminants can be flushed out or purged by briefly activating a reverse flow system (e.g., once every few days). As illustrated in FIG. 1A, the reverse flow system may be activated by opening a two-way purge valve 142 which sends warm nitrogen down a short purge line 152 directly into heat exchanger section 146 just above flow restrictor 148. At the same time that two-way purge valve 142 is opened, three-way valve 138 is switched so that the warm nitrogen entering the bottom of heat exchanger section 146 flows up the heat exchanger section 146 and out through exhaust outlet 154. As the warm nitrogen flows up heat exchanger section 146, it evaporates any condensed carbon dioxide and eventually, near the top of the heat exchanger, drives out any adsorbed moisture, too. It has been found that a purge of two to three minutes is sufficient to desorb any contaminants that had been trapped in the line during a 24 hour run. The warm purge line 152 is also brazed at 156 to the nitrogen supply line just upstream from opening 149. When the purge is activated, the nitrogen warms this terminal region of the nitrogen supply line and desorbs and blows out any contaminants restricting the flow there, thus "defrosting" the nitrogen supply line and expansion capillary.

This reverse flow "defrost" is similar in some respects to the operation of a regenerator in a large industrial liquefier. In these liquefiers the incoming air is passed through a regenerator consisting of two columns containing insulated stacks of metal or other material of large surface area. Gas flow is directed down one column, after which the gas is cooled by expansion, and then up the other. The flow is reversed every minute or two. The cooled filling in one column then pre-cools the incoming gas on the next cycle. At the same time contaminants such as water or carbon dioxide adsorb on the material in the column and are desorbed and blown out of the column on the next cycle. In contrast, in the small liquefier described in FIG. 1A, the flow rates are small enough that one can operate the liquefier continuously for long periods of time and only defrost it occasionally. The defrost, or purge, can be done manually, or automatically with appropriate electronic controls.

In a preferred embodiment a flow-rate restricting choke 143 is inserted in the purge line immediately after purge valve 142. This causes the incoming purge stream to drop in pressure and increase in volume for the same mass flow through the pressure swing absorber, allowing it to maintain a higher level of purity of the nitrogen feed.

A hygrometer 158 may be incorporated into the device to facilitate trouble-free operation without human intervention, a feature which is important in an environment where no technical help is readily available. The hygrometer 158 is preferably low in cost and is connected to the permeate side of the membrane nitrogen separator 136. On start-up, the air entering the membrane separator 136 will contain some moisture until the pressure swing absorber drier has become fully conditioned. Most of this moisture permeates through the walls of the membrane fibers of the separator 136, but some continues on and would pass through the 3-way valve 138 into the nitrogen supply line and contaminate it if this valve were open. This is prevented by using the hygrometer 158 to measure the moisture content of the permeate flow from the separator 136 out of a check valve 160, and to keep the nitrogen 3-way valve 138 closed until the nitrogen moisture content falls below a pre-determined value. By controlling the flow of gas to the second section of the gas supply system in dependence upon a level of gas purity detected by the hygrometer, this reduces clogging of the low-temperature portions of the gas supply line. It may be noted that, because of the drying effect of the membrane separator 136, the moisture content of the permeate flow at 160 is much higher than that of the nitrogen product flow. Furthermore, the permeate is at ambient pressure rather than at the high pressure at the input. Thus, a simple, low cost hygrometer can be used, rather than a high pressure, high sensitivity sensor for this purpose. Check valve 160 prevents moist ambient pressure air from entering the hygrometer 158 when the system is not working.

An electronic or other depth gauge 162 is used to measure the quantity of liquid nitrogen in the dewar and to indicate to a user whether sufficient liquid nitrogen has been produced and collected in the dewar. The liquid nitrogen can be dispensed from the device by opening a dispense valve 140. With this valve open, nitrogen gas passes through a pressure regulator 164 that drops the air pressure from about 791 kPa (100 psig) to about 136 kPa (5 psig). The lower pressure nitrogen then enters the dewar and pressurizes the gas in the dewar, forcing liquid nitrogen up the dispense line 167 through the check valve 168, which is set at about 13.8 kPa (2 psi) cracking pressure, to the user's container. The flow restricting valve 166 on the top of the dewar is sized to permit the passage of the small flow of nitrogen gas during pre-cooling and liquefaction, but not the larger flow during the dispensing of the liquid nitrogen.

Figure 1B:
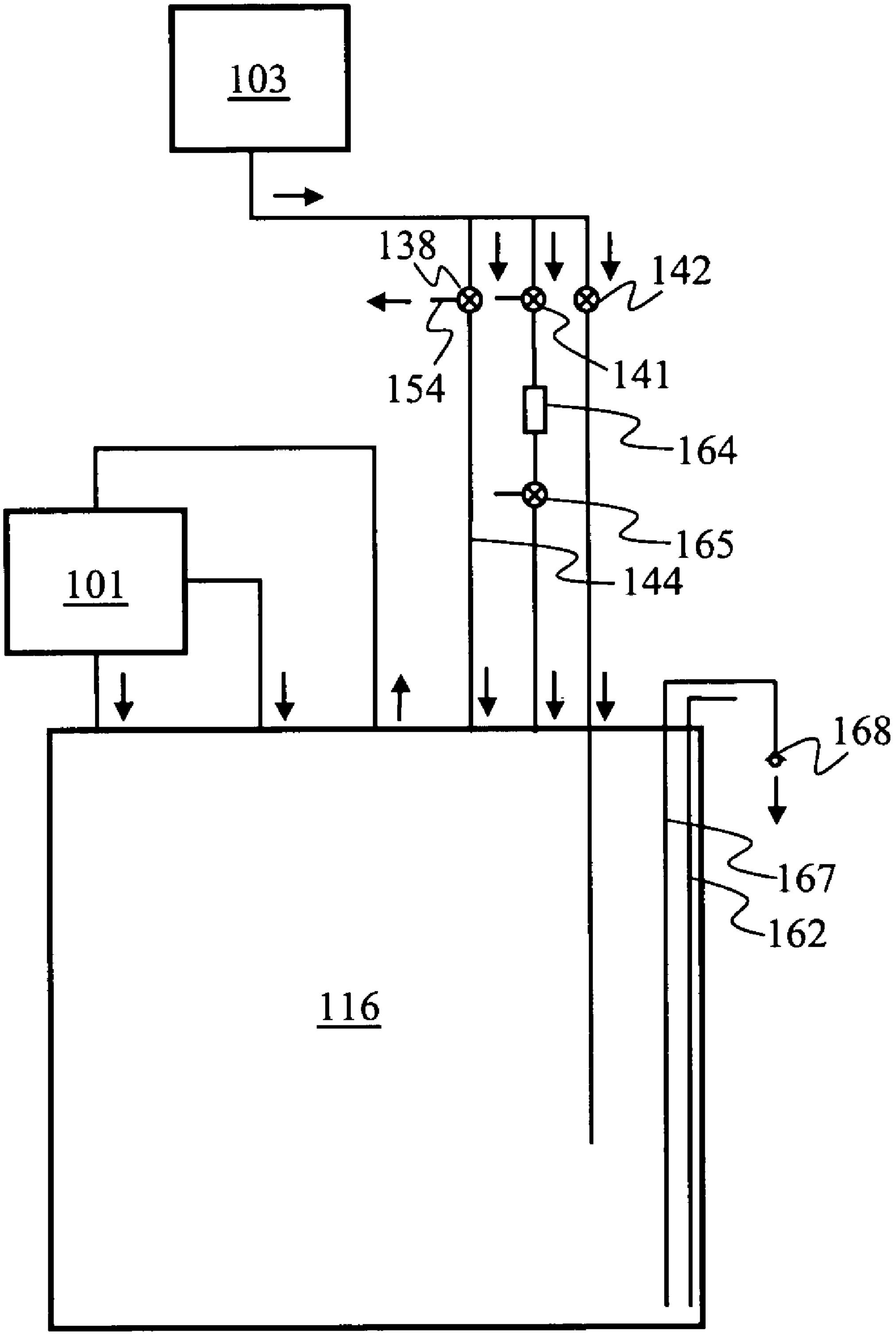
FIG. 1B is a schematic of a device for the liquefaction of nitrogen, according to another embodiment of the invention.

In an alternate embodiment, as shown in FIG. 1B, a poppet-type quick exhaust valve 165 is used in place of check valve 166 (FIG. 1A). Valve 165 is positioned with its inlet port connected to the regulator 164 and its outlet to the top of the dewar 116. The exhaust port of the exhaust valve 165 is open to atmosphere. In addition, in this embodiment two-way valve 140 (FIG. 1A) is replaced with a normally closed, three-way valve 141. When the dispense button is activated, valve 141 is activated and the inlet port of the quick exhaust valve 165 is pressurized, causing the poppet to close its exhaust port, pressurize the dewar, and cause LN2 to be dispensed. Upon release of the dispense button, valve 141 is de-activated and the gas in the dispense line is vented through the exhaust port of 3-way valve 141. Pressure in the dewar then forces the poppet away from the exhaust port, allowing the pressurized dewar to vent to atmosphere. In this embodiment very little gas is needed to dispense a given amount of LN2 as gas is not vented during the transfer as it would be were check valve 166 (FIG. 1A) to be used instead. The smaller amount of gas used reduces the mass flow through the pressure swing absorber, allowing it to maintain a higher level of purity of the nitrogen feed. This prevents a bleed through of moist air during the dispense process.

Because liquid nitrogen, liquid oxygen, and other cryogens can inflict severe frostbite when brought into contact with the skin, it is preferable that the device includes safety and security features.

Figure 2:
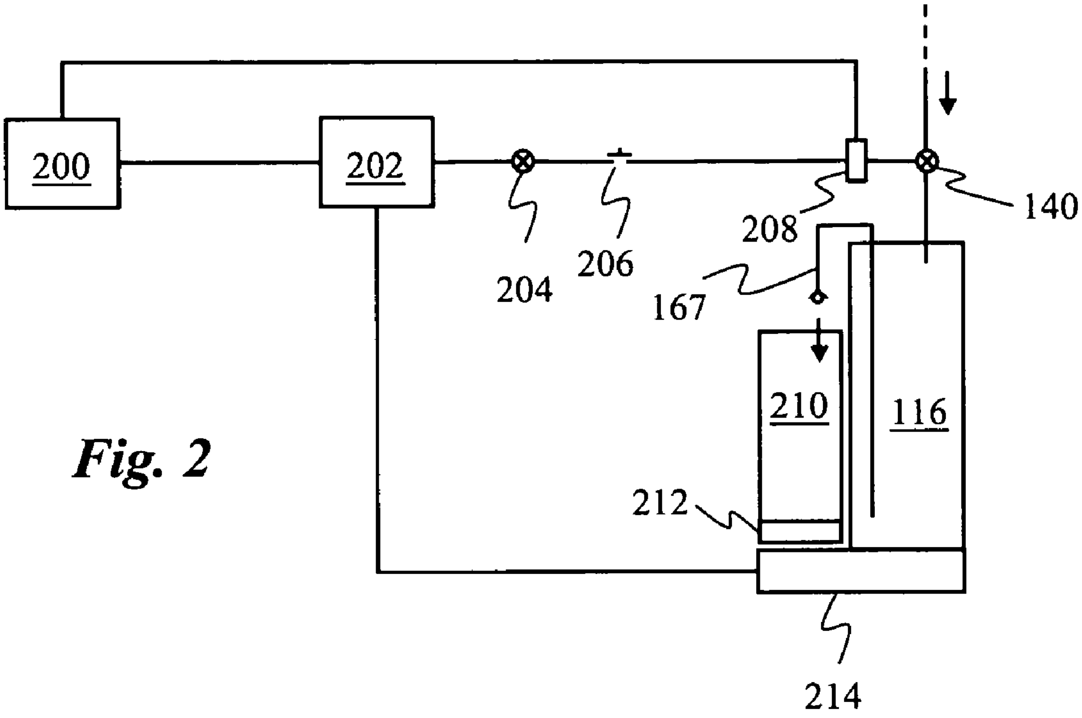
FIG. 2 is a schematic of a device for the liquefaction of nitrogen including an interlock mechanism for additional safety, according to an embodiment of the invention.

The dispense valve 140 (FIG. 1A) may be easily activated by a push-button on the side of the liquefier. However, in order to prevent unauthorized personnel dispensing the liquid nitrogen or children from being exposed to the liquid nitrogen, a key lock may be incorporated in the circuit to the dispense valve 140, as shown in FIG. 2. The key lock prevents the dispense valve from opening when locked and allows the dispense valve to be opened when unlocked by a user key. A power supply 200 is connected in series with a key lock 204, push-button 206, and solenoid 208, which controls dispensing valve 140. Provided key lock 204 is enabled with a key (e.g., physical key, code-activated keypad, or RFID key attached to authorized user), a user may depress push-button 206 to open dispense valve 104, which forces liquid nitrogen from the dewar 116 through dispensing line 167 as described earlier in relation to FIG. 1A.

As a further precaution, an interlock may be provided that senses the presence of the user dewar 210. If the user dewar 210 is not in correct position under the liquid nitrogen outlet line 167, a relay 202 in the valve control circuit does not permit the valve 140 to be opened. The interlock can be accomplished with various proximity sensing techniques in which a proximity sensor 214 connected to relay 202 is able to detect the physical proximity of the user dewar 210, and activates relay 202 only when dewar 210 is in correct dispensing position. Thus, the proximity sensor prevents the dispense valve from opening when a dispense dewar is not sensed and allows the dispense valve to be opened when a dispense dewar is sensed. Typically, the dewar 210 will have a sensible component 212 attached to it that is able to activate proximity sensor 214. For example, sensor 214 may be a Hall effect switch and component 212 may be a magnet on the base of the dewar. Alternatively, in a preferred interlock, the component 212 is a radio frequency identification (RFID) tag carrying a unique code and the proximity sensor 214 is an RFID transponder situated under the dewar stand. If the transponder 214 does not detect an RFID with the correct code, the relay 202 remains open, preventing the dispense valve 140 from opening.

In addition to these active safety and security features, appropriate notices warning of the dangers of the use of these cryogens should still be posted immediately adjacent to the dispense push-button 206 and liquid nitrogen outlet line 167.

Figure 3:
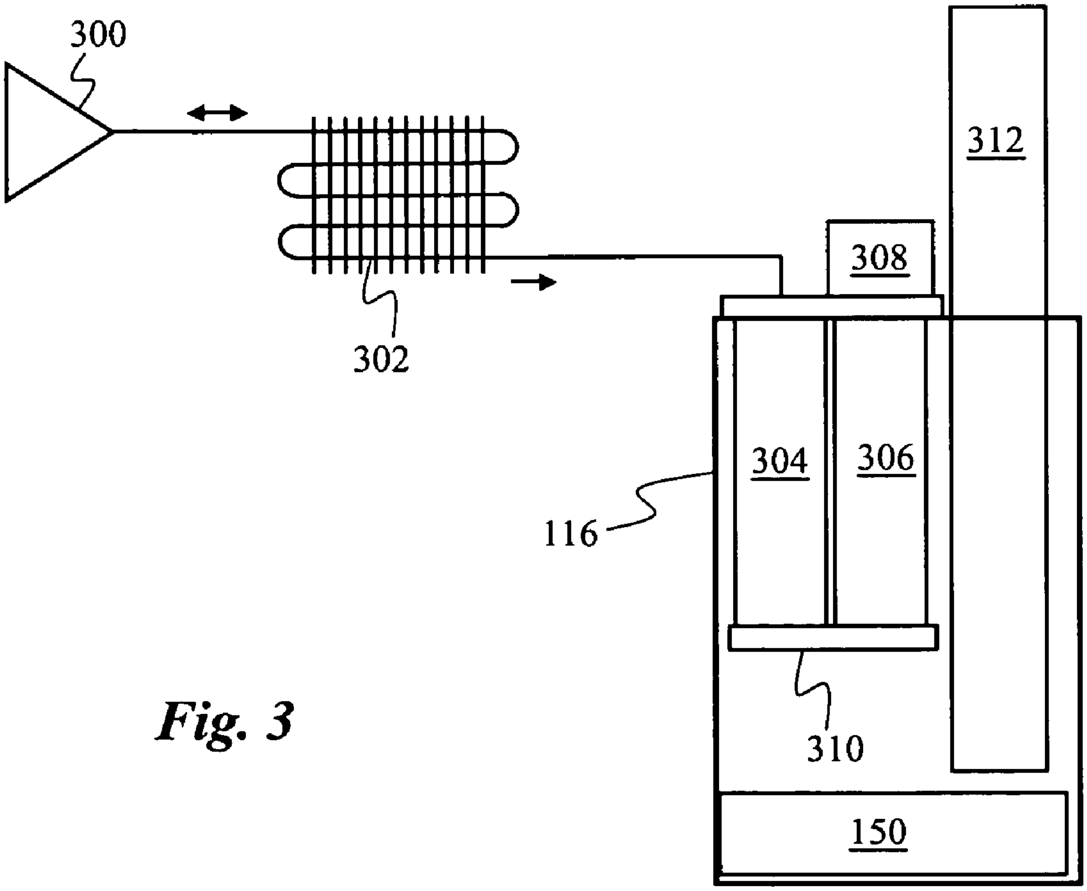
FIG. 3 is a schematic of a device for the liquefaction of nitrogen using a pulse-tube cryocooler, according to another embodiment of the invention.

In another embodiment of the invention, the liquefier is designed using a pulse-tube type cryocooler instead of a Kleemenko cryocooler. For example, FIG. 3 shows a small scale gas liquefier based on a pulse-tube design. For simplicity of illustration, only the pulse-tube refrigeration cycle components of the device are shown in detail in the figure. The other components of the liquefier (e.g., nitrogen circuit 312) and their operation are the same as shown in FIGS. 1 and 2. A oscillatory pressure compressor 300 pumps refrigeration fluid in forward and reverse directions through a refrigeration line which connects compressor 300 to after-cooler 302 and a pulse tube assembly entering the dewar 116. The pulse tube assembly includes a pulse tube regenerator 304, a pulse tube 306, both of which are connected to a cold end heat exchanger 310 which, like evaporator 125 in FIG. 1A, supplies cooling to liquefy nitrogen flowing in nitrogen circuit 312 to produce liquid nitrogen 150. Helium is usually chosen for the working fluid but nitrogen could be used for the liquefaction of gases with normal boiling points above 100 K. For details see the article "A Short History of Pulse Tube Refrigerators" by Peter Kittel at <http://ranier.oact.hq.nasa.gov/Sensors_page/Cryo/CryoPT/CryoPTHist.html>.

In the case of an oxygen liquefier, separate liquefaction and refrigerant dewars are preferably used for safety reasons in order to keep the refrigerant lines, which contain flammable hydrocarbons, physically separated from the liquid oxygen. A thermally conductive component connecting the separate dewars allows the refrigeration cold plate in the first dewar to cool the load in the other dewar. Alternatively, a casing may be provided to seal off the refrigeration lines from the oxygen. In any case, although the refrigeration lines may be physically isolated from the oxygen lines and oxygen, they are thermally coupled and thus are, in effect, within the same thermal region regardless of whether the region is implemented as one dewar or two thermally coupled dewars.

The invention claimed is:

1. A device for liquefaction of a gas, the device comprising:

a thermally insulated region in which the gas is liquefied and collected, a gas supply system comprising a first section outside the thermally insulated region and a second section within the thermally insulated region, wherein the first section provides a purified stream of gas to a gas supply line in the second section, a cryogenic refrigerator comprising a warm section outside the thermally insulated region and a cold section inside the thermally insulated region, wherein the cold section is thermally coupled to the second section of the gas supply system to cool the purified stream of gas, a dispensing line comprising an input end within the thermally insulated region and an output end outside the thermally insulated region, wherein:

the first section of the gas supply system comprises a compressor to compress the gas so that the purified stream of gas has a high pressure above atmospheric pressure;

the cold section of the cryogenic refrigerator has a minimum temperature above a boiling point of the gas at atmospheric pressure and below a boiling point of the gas at the high pressure, the second section of the gas supply system comprises a flow restrictor where the pressure drops from the high pressure to atmospheric pressure and a portion of the purified stream of gas evaporates, cooling a fraction of the purified stream of gas to the boiling point of the gas at atmospheric pressure.

2. The device of claim 1 wherein the cryogenic refrigerator is a pulse-tube cryogenic refrigerator.

3. The device of claim 1 wherein the cryogenic refrigerator is a Kleemenko-cycle cryogenic refrigerator.

4. The device of claim 1 wherein the cold section of the cryogenic refrigerator comprises a counter-current heat exchanger comprising a first heat exchanger and a second heat exchanger, and wherein the second section of the gas supply system comprises a heat exchanger section thermally coupled to the counter-current heat exchanger.

5. The device of claim 1 wherein the second section of the gas supply system comprises a warm purge line connected to a cold end of the gas supply line, wherein the first section of the gas supply system comprises a purge valve controlling a flow of warm gas into the warm purge line and a three-way valve allowing the warm gas to flow upward through the gas supply line and vent.

6. The device of claim 1 wherein the first section of the gas supply system comprises a pressure swing absorber, a membrane separator, a hygrometer connected to the membrane separator, and a valve connected to the hygrometer to control the flow of gas to the second section of the gas supply system in dependence upon a level of gas purity detected by the hygrometer.

7. The device of claim 1 wherein the first section of the gas supply system comprises a dispense valve that allows pressurized gas to flow into the thermally insulated region and a pressure regulator that reduces a pressure of the gas prior to entering the thermally insulated region.

8. The device of claim 7 further comprising a key lock connected to the dispense valve, wherein the key lock prevents the dispense valve from opening when locked and allows the dispense valve to be opened when unlocked by a user key.

9. The device of claim 7 further comprising a proximity sensor connected to the dispense valve, wherein the proximity sensor prevents the dispense valve from opening when a dispense dewar is not sensed and allows the dispense valve to be opened when a dispense dewar is sensed.

10. A method for liquefaction of a gas, the method comprising:

purifying the gas in a first section of a gas supply system to produce purified gas, cooling the purified gas in a second section of the gas supply system to produce condensed gas, collecting the condensed gas in a thermally insulated region, and dispensing the condensed gas from the thermally insulated region through a dispensing line, wherein cooling the gas comprises reducing the temperature of the gas using a cryogenic refrigerator having a minimum temperature above a boiling point of the gas at atmospheric pressure and below a boiling point of the gas at the high pressure, and wherein the method further comprises compressing the gas so that the purified gas has a pressure above atmospheric pressure, expanding the condensed gas to atmospheric pressure to evaporate a portion of the condensed gas and cool a fraction of the condensed gas to the boiling point of the gas at atmospheric pressure.

11. The method of claim 10 wherein the cryogenic refrigerator is a pulse-tube cryogenic refrigerator.

12. The method of claim 10 wherein the cryogenic refrigerator is a Kleemenko-cycle cryogenic refrigerator.

13. The method of claim 10 wherein the cryogenic refrigerator comprises a counter-current heat exchanger and reducing the temperature of the gas comprises thermally coupling the gas to the counter-current heat exchanger.

14. The method of claim 10 further comprising intermittently opening a purge valve allowing the purified gas to flow through a warm purge line, sending the warm gas from the warm purge line upward through a cold end of a gas supply line, and venting the warm gas from the gas supply line out through a three-way valve.

15. The method of claim 10 wherein purifying the gas comprises passing the gas through a pressure swing absorber and a membrane separator, sensing a level of gas purity at the membrane separator, and controlling the flow of purified gas in dependence upon a sensed level of gas purity.

16. The method of claim 10 wherein dispensing the condensed gas comprises opening a dispense valve that allows gas to flow into the thermally insulated region and reducing a pressure of the gas prior to entering the thermally insulated region.

17. The method of claim 10 wherein dispensing the condensed gas comprises requiring a user key to enable dispensing.

18. The method of claim 10 wherein dispensing the condensed gas comprises sensing a proximity of a dispense dewar and requiring a sensed presence of the dispense dewar to enable dispensing.

* * * * *